US007416746B2

(12) United States Patent
Grandics et al.

(10) Patent No.: US 7,416,746 B2
(45) Date of Patent: Aug. 26, 2008

(54) METHOD FOR CANCER THERAPY USING HERBAL EXTRACTS

(76) Inventors: Peter Grandics, 5922 Farnsworth Ct., Carlsbad, CA (US) 92008; Joe K. Holbrook, Sr., 139 Shannon Lee, San Antonio, TX (US) 78216

( * ) Notice: Subject to any disclaimer, the term of this patent is extended or adjusted under 35 U.S.C. 154(b) by 0 days.

(21) Appl. No.: 11/627,655

(22) Filed: Jan. 26, 2007

(65) Prior Publication Data

US 2007/0166390 A1 Jul. 19, 2007

Related U.S. Application Data

(63) Continuation-in-part of application No. 10/670,131, filed on Sep. 22, 2003, now Pat. No. 7,201,924, which is a continuation-in-part of application No. 10/227,006, filed on Aug. 23, 2002, now abandoned, which is a continuation-in-part of application No. 09/949,126, filed on Sep. 7, 2001, now abandoned.

(51) Int. Cl.
*A61K 36/00* (2006.01)
*A61K 36/20* (2006.01)
*A61K 35/73* (2006.01)
*A61K 33/04* (2006.01)

(52) U.S. Cl. .................. 424/725; 424/535; 424/765; 424/705; 424/725.1

(58) Field of Classification Search ............... None
See application file for complete search history.

(56) References Cited

U.S. PATENT DOCUMENTS

2001/0024664 A1* 9/2001 Obukowicz et al. ......... 424/725
2002/0132021 A1* 9/2002 Raskin et al. ............... 424/773

FOREIGN PATENT DOCUMENTS

JP 01/0090129 4/1989
JP 97/0303079 11/1997

OTHER PUBLICATIONS

A United Kingdom patent by Doyle et al., Patent Specification No. 864,740. entitled "A Pharmaceutical Substance for the Treatment of Carcinoma . . . ," issued on Apr. 6, 1961.
B.R. Cassileth et al., "Survival and Quality of Life Among Patients Receiving Unproven as Compared with Conventional Cancer Therapy," New Engl. J. Med. 324: 1180-1186 (1991).
R. Doll et al., "Mortality in Relation to Smoking: 22 Years' Observations on Female British Doctors," Br. Med. J. 280: 961-971 (1980).
R. Doll & A. Hill, "Lung Cancer and Other Causes of Death in Relation to Smoking," Br. Med. J. 2: 1071-1081 (1956).
A.M. Marchevsky, "Malignant Epithelial Tumors of the Lung" in Surgical Pathology of Lung Neoplasms (A.M. Marchevsky, ed., New York, Marcel Dekker, 1990), pp. 77-229.

An internet article entitled "Search for Divine Somarasa Plant," 2001, Indian Express Newspapers (Bombay) Ltd., 3 pages.
An internet article, P. Wilson, entitled "Ploughing the Clouds: The Search for Irish Soma," 1999, 2 pages.
An internet review article on the book entitled "Soma: The Divine Hallucinogen," by D. Spess, downloaded Mar. 2002, 3 pages.
An internet article, M. Smith, entitled "Amanita Muscaria as the God/Plant Soma of Rigveda," downloaded Mar. 2002, 5 pages.
An internet review article entitled "Soma: Divine Mushroom of Immortality," written by R.G. Wasson in 1968, 2 pages.
An internet article entitled "Soma: The Mushroom God," downloaded Mar. 2002, 3 pages.
An internet article entitled "Soma," downloaded Mar. 2002, 2 pages.
An internet article, R. Rudgley, entitled "Soma from the Encyclopedia of Psychoactive Substances," 1998, 3 pages.
An internet article, T. McKenna, entitled "What Is Soma?," downloaded Mar. 2002, 2 pages.
P. Lissoni et al., Neuroendocrinol. Lett. 79: 350-357 (2001).
A publication, "Cancer Facts and Figures—2002," American Cancer Society, Atlanta, 2002.
T. Thar et al., "Radiation Treatment of the Carcinoma of the Cervix," Semin. Oncol. 9: 299-311 (1982).
V.T. Devita et al., "Perspectives in Research in Gynecologic Oncology," Cancer 38: 509-525 (1991).
D.S. Alberts et al., "Cisplatin in Advanced Cancer of the Cervix: An Update," Semin. Oncol. 18: 11-24 (1991).
F. Petterson et al., "Carcinoma of the Uterine Cervix" in Annual Report on the Results of Treatment in Gynecological Cancer, FIGO 22: 51-63 (1994).
R.T.H. Griffith, "The Hymns of the Rigveda" (J.L. Shastri, ed., Motilal Banarsidass Publishers, 1999).
P. Grandics, "Cancer: A Single Disease with a Multitude of Manifestations," J. Carcinogenesis 2: 9 (2003).
Grandics, P., "Cancer: A single disease with a multitude of manifestations," J. Carcinogenesis, 2 (2003).
Mulholland, J., "Soma: An attempt to classify the plant and the drug," Soc. Sci. Med. 148: 181-184 (1980).
McDonald, A., "A biological perspective on the identity of Soma (Nelumbo nucifera gaertn.) Based on scriptural and iconographic records," Econ. Bot. 58: S147-S173 (2004) (abstract only).
Madhihassan, S., "Soma as energizer-cum-euphoriant, versus Sura, as intoxicant," Ancient Sci. Life 3: 161-168 (1984).
Thas, J. J., "Preliminary pharmacological findings on *Ceropegia juncea*," Planta Med. 39: 242 (1980).

* cited by examiner

*Primary Examiner*—Christopher R. Tate
(74) *Attorney, Agent, or Firm*—Catalyst Law Group, APC; Michael B. Farber

(57) ABSTRACT

A new method is described for the treatment of cancer. In one alternative, the method utilizes two main compositions. The first composition is Soma, a healing herb described in the Rig Veda, the sacred scriptures of the Hindus. The second composition is a composite of plant-derived substances and a mineral. When they are administered to cancer patients following the recommended therapeutic regimen, regression of the cancer results. Alternatively, the second composition can be used alone.

34 Claims, No Drawings

METHOD FOR CANCER THERAPY USING HERBAL EXTRACTS

CROSS-REFERENCES

This application is a continuation-in-part of application Ser. No. 10/670,131 by Grandics et al., filed on Sep. 22, 2003 now U.S. Pat. No. 7,201,924 and entitled "Method for Cancer Therapy Using Herbal Extracts," which is a continuation-in-part of application Ser. No. 10/227,006 (now abandoned), by Peter Grandics, filed on Aug. 23, 2002 and entitled "Method for Cancer Therapy Using Herbal Extracts," which in turn was a continuation-in-part of application Ser. No. 09/949,126 (now abandoned) by Peter Grandics, filed Sep. 7, 2001, and entitled "Method for Cancer Therapy Using Herbal Extracts." The contents of application Ser. Nos. 10/670/131, 10/227, 006, and 09/949,126 are all incorporated herein in their entirety by this reference.

BACKGROUND OF THE INVENTION

This invention is directed to herbal compositions for treating cancer as a disease with an inflammatory component and to methods employing these compositions.

General Background and State of the Art: It is a widely accepted view that cancer can start in just one of the body's billions of cells. Cancer could be triggered by a variety of factors. Our current thinking is that radiation, toxic chemicals, viruses or other infectious agents may induce an error in the transcription of the cell's genetic information. The cells then divide to form abnormal cells, without normal genetic controls. The immune system of the body then fails to respond properly by not destroying the aberrant cells. The aberrant (cancerous) cells lose their normal controls of cell division and continue to proliferate. This leads to the formation of a growing mass or tumor expanding into healthy tissues. The cancerous cells compete with normal cells for nutrition. Also, the cancerous cells may migrate into the bloodstream or the lymphatic system that is the primary cause of the formation of a metastasis.

It is currently believed that cancer could be reversed if the altered genetic message of the cell could be corrected. However, such a method up to this date has not been developed. Our current mainstream treatment methods focus exclusively on the tumor and equate cancer with the cancerous lesion(s) appearing in these patients. This way cancer is considered a localized phenomenon that may lead to an incomplete definition of this disease.

The mainstream treatment modalities for cancer are sometimes described as the cut, burn and poison therapies. As the cancerous lesion is equated with cancer, its surgical removal, whenever is possible, is considered indispensable. This is done despite the evidence that surgery fails to correct the underlying cause of cancer and may actually cause the spreading of cancer. Residual lesions are treated with radiation and chemotherapy, both of which produce severe side effects. These treatments are immunosuppressive and can pave the way to secondary infections, an important cause of mortality following chemotherapy.

Toxicity to the kidneys, bone marrow and the nervous system may produce lasting complications even if a remission is achieved. It is also established that such therapies can actually cause secondary tumors. Regardless of the practice of these cancer treatments, two-thirds of all cancer patients eventually die of the disease. Moreover, many of the malignant tumors are resistant to these conventional treatments.

A safe and effective cancer treatment has been the goal of scientists for many decades. Such a technique must be selective in destroying the cancer cells without irreversibly damaging normal cells. It is well established that cancer is continually produced in the human body but is kept in check by the immune system. Only when the immune system is weakened can cancer establish itself. Therefore, it would be desirable to develop methods that restore the healing ability of the body so cancer would be eliminated naturally by the immune system.

INVENTION SUMMARY

Pursuant to this invention a new technique is described to treat cancer. In an illustrative embodiment, an inoperable, malignant lung cancer was treated with a plant extract called Soma, and an adjunct second therapeutic modality comprised of a mixture of natural plant derived substances and a mineral. The Soma and the adjunct second therapeutic modality can be used together; alternatively, the second adjunct therapeutic modality can be used alone.

Methods according to the present invention are particularly suited to the treatment of malignancies of the lymphoid system.

DETAILED DESCRIPTION OF THE PREFERRED EMBODIMENTS

Interest in alternative therapies is increasing as dissatisfaction with traditional therapies grows. The absence of markedly improved treatments despite decades of research, the toxicity of chemotherapy and the lack of significant improvement in cure rates for the major cancers contribute to the dissatisfaction (Cassileth et al. (1991) New England Journal of Medicine 3249 (17) 1180-1185). This led to an increasing interest even within the traditional medical community for alternative cancer treatments.

The present invention describes an alternative therapy for cancer. We offer a new theory for the development of this disease that describes cancer as an endocrine disease. More specifically, we hypothesize that cancer manifests as a result of the malfunctioning of the pituitary gland that resides at the apex of the endocrine system. Pituitary hormones regulate the functions of other glands, e.g., the thyroid, the adrenals or the pancreas. A dysfunctional pituitary gland manifests in the weakening of the immune system and eventually in its inability to eliminate cancerous cells.

This hypothesis proposes that cancers arise from a single cancer "progenitor" cell that gives rise to all known forms of cancer. This cell is part of the working mechanism of the immune system and normally resides in the sinus cavity from which it is mobilized as needed. These cells are eliminated by specific activated lymphocytes after they complete their tasks. When the elimination of these cells is unsuccessful due to weakened thyroid, adrenal, and pancreatic activities, viable damaged cells remain that can attack host tissue. These cells will seek out injury sites inside the body that are present due to physical damage, the activities of pathogenic organisms, parasites, chemical agents, or irradiation and establish colonies at those locations. The final morphology of the cancer cells develops as a result of interactions with the surrounding host tissue.

Secretions of the thyroid and adrenal glands and the pancreas play a critical role in the activation of the killer cell capable of eliminating cancer "progenitor" cells as well as established tumors.

The described natural formulas are intended to optimize the functioning of the pituitary gland as well as the other three endocrine glands leading to the restoration of normal immune functions. The effect of the formulas results in the regression of cancerous growth without the side effects of contemporary therapies.

A potential causative agent for cancer, besides the environmental factors, is prolonged periods of stress. Stress has been found to be associated with immunosuppression and an increased frequency of tumors (Lissoni, P. et al. Neuroendocrinol. Lett. (2001) 79, 350-357). Therefore, it is important that life-style changes also accompany any therapeutic intervention if long-term results are sought.

The following compositions are described in the subject invention.

In one embodiment of the invention, two compositions are used.

In this alternative, the first composition is an extract of the Soma plant. Soma is the famous healing plant described in the sacred scriptures of the Hindus, the Rig Veda (Griffith R T H, The hymns of the Rigveda, Shastri, J L ed. Delhi, Motilal Banarsidass Publishers, 1999). Since the passing of the Vedic era, many investigator sought to identify this mystical herb to which religious tradition attributes many great healing powers.

As a result, today Soma is mainly believed to be the hallucinogenic mushroom, *Amanita muscaria*. However, Indian scientist Dr. S N Paddhy from the Department of Botany, Orissa Government Science College challenged this view and stated that the actual Soma plant was neither hallucinogenic nor intoxicating, but kept its consumers awake and alert (The Indian Times, Feb. 11, 2001). He pointed out that the identification of Soma as *Amanita muscaria* is in conflict with the Vedic principles, its reported mode of action, as well as the description of the plant in the scriptures. The Soma plant is said to have milky secretions, a creeper-like appearance, and exists in two varieties according to the Rig Veda. We concur with Dr. Paddhy's analysis on Soma. Accordingly, the botanical identification of the Soma plant is *Asclepias tuberosa*.

In one alternative, Soma extract was prepared following the general recommendations in the 9th Book of Rig Veda with some modifications. More specifically, the root of the mature Soma plant was harvested and cleaned in water. The roots were cut into small pieces and placed in a wooden bowl with water added for extraction of the active ingredients. The roots were crushed with a stone pestle while soaked in water. The crushed mixture was placed in a glass bottle and allowed to sit for a month. Salt is added to the mixture as preservative. Subsequently, the mixture was filtered to remove insoluble materials. Soma extract is stored refrigerated. Alternatively, Soma extract is commercially available from A-D Research Foundation (Carlsbad, Calif.).

In a preferred alternative, the minced roots of *Asclepias tuberosa* are steeped in boiling water for about 20 minutes to inactivate potentially toxic proteins. The roots are filtered and the supernatant is used as a therapeutic.

The other component of this first embodiment of the subject invention is a mixture of plant-derived and mineral substances, called MSQ-11. More specifically, the active ingredients are blackstrap molasses, apple cider vinegar, quinine, and sulfur. The optimal composition is made up as follows:

Thoroughly mix in a blender the following ingredients in this order:
1. 755 ml blackstrap molasses,
2. 59 ml apple cider vinegar,
3. 3 g quinine (USP grade),
4. 29 g of sulfur (USP grade).

Blend on high speed, and add sufficient whole milk to bring the final volume to 1 quart (946 ml). The mixture is stored refrigerated. For long-term storage, it must be kept in a freezer. Additional optional ingredients are Vitamin $B_{12}$ (63 mg), folic acid (250 mg), and rose petal extract/rose oil (50 .mu.l) dissolved in the final quart. One or more of these optional ingredients can be used. The formula including Vitamin $B_{12}$ and rose oil is designated MSQ-11A. For milk-intolerant patients, such as patients with lactose intolerance, the milk in the formula can be replaced by purified water.

In this first embodiment, to treat malignancies of the lymphoid system, the formula is complemented with the following additions and called MSQ-12.
1. ½ tsp of ground red pepper,
2. 2 tbsp of corn oil,
3. 177 ml of fresh squeezed pineapple juice,
4. 87 g of finely ground raw almonds, and
5. 2 aspirins a day taken separately by the patient.

The MSQ-11 formula can be used on its own if iodine (USP 23, Strong Iodine Solution) is added to the composition in the amount of 6-9 ml per 1 quart (946 ml) final volume that is equivalent to 4-6 drops per 30 ml single dose. This formula is called MSQ-13

In this first embodiment, Soma is taken orally once a day, preferably one hour before bedtime. The recommended dosage is 1 ml dispersed into a cup of water. Soma should be taken for a month at this dosage. For the next month, it should be taken every other day. A weeklong break in the schedule is then recommended. The dosing is resumed at a rate of 0.5 ml per day for one month and the same dosage taken every other day for the next month.

In this first embodiment, the composite mixture (MSQ-11, MSQ-12 or MSQ-13) is administered orally at a dose of 1-3 tbsp (15-45 ml) for adults, preferably at 2 tbsp, three times a day taken with meals. Along with this treatment, 6 glasses of water should be taken daily spaced at proper intervals. This administration schedule is followed for 3-4 weeks. The administration of this therapy may continue depending on the rate of cancer regression. The therapy can be used prophylactically after remission is obtained.

When used in conjunction with chemotherapy, Soma has largely relieved chemotherapy-associated nausea and vomiting. Patients taking Soma were able to carry on with their normal activities shortly after the administration of the chemotherapeutic agents. In one patient, Soma has shown some degree of protection against the nephrotoxicity of Cisplatin. Accordingly, compositions according to the present invention can be used in conjunction with chemotherapy in order to relieve chemotherapy-associated nausea or vomiting.

As used herein, the term "therapeutic effect against cancer" means any effect against cancer, including but not limited to symptomatic relief, improvement in subjective well-being, histological improvement such as reduction in tumor burden, reduction in stage or grade of the tumor, reduction of tissue damage associated with malignancy, or other biological, pathological, or histological effects.

In another embodiment of the composition, Soma is not used. Instead, the compositions described above as MSQ-11, MSQ-12, or MSQ-13 are administered. In this embodiment, the composite mixture (MSQ-11, MSQ-12 or MSQ-13) is administered orally at a dose of 1-3 tbsp (15-45 ml) for adults, preferably at 2 tbsp, three times a day taken with meals. Along with this treatment, 6 glasses of water should be taken daily spaced at proper intervals. This administration schedule is followed for 3-4 weeks. The dosage can be adjusted as needed depending on the response of the patient. The administration of this therapy may continue depending on the rate of cancer regression. The therapy can be used prophylactically after remission is obtained.

Another aspect of the present invention is a method of treating cancer comprising administering a composition or compositions according to the present invention to a patient in need thereof. The compositions administered can include Soma. Alternatively, the composition can be one of MSQ-11, MSQ-12, or MSQ-13, without Soma. If the composition is a composition according to the present invention including ground red pepper, corn oil, pineapple juice, and raw almonds, the method preferably further comprises administering aspirin to the patient.

The malignancy to be treated can be, but is not necessarily limited to, a malignancy of the lymphoid system.

The following Examples illustrate the advantages of the subject invention. These Examples are illustrative only and are not intended to limit the invention. Accordingly, it is to be understood that the description in this disclosure is to facilitate comprehension of the invention and should not be construed to limit the scope thereof as persons skilled in the art can, in light of this disclosure, generate additional embodiments without exceeding the scope or departing from the spirit of the claimed invention.

EXAMPLE 1

Resolution of Pleuritis Carcinomatosa and Atelectasis in an Inoperable Malignant Lung Cancer A 55-year-old male patient was admitted to the hospital on Oct. 27, 1999 with right-sided chest pain, hemoptysis, worsening shortness of breath, and dyspnea on exertion.

He had a history of smoking for 40 years, 1.5-2 packs a day. He claimed that he consumed 1 glass of wine and 2 bottles of beer a day. He suffered myocardial infarction in May 1999. On physical exam he was an obese man who appeared older than his chronological age. Chest and throat exam revealed emphysema and severe chronic laryngitis. Cardiac enlargement and hepatomegaly was observed. Extremities were free of edema and clubbing.

His blood gases on room air were $pO_2$ 61.9, $pCO_2$ 52.6, pH 7.39 and Sat 91%. A CT of the chest revealed a large mass in the third segment of the right lung that propagated onto the pleura. Around the mass, distelectasis and infiltration was observed. Pleural fluid or abnormal lymph nodes were absent.

A biopsy was performed and the initial finding was a partially undifferentiated squamous cell carcinoma. Due to the patients cardio-respiratory status and the extent of the infiltration, the tumor was evaluated as inoperable. The exact size of the tumor could not be determined.

He was placed on a Carboplatin and Vepesid combination chemotherapy and radiation therapy. He received 2 cycles of chemotherapy and 30 Gy of irradiation. A chest CT taken on Mar. 3, 2000 had shown the presence of a 5 cm diameter tumor in the upper right lobe that contained an irregular internal cavity, and showed propagation onto the pleura. In April 2000, the patient decided to discontinue the therapies due to their severe side effects.

Starting in June 2000, the patient has taken a one month long course of the oral combination herbal supplement, MSQ-11. The active ingredients are molasses, apple cider vinegar, quinine and sulfur. The dosage was 3×1 tablespoons a day taken with meals until 1 quart of the mixture was consumed. Ample consumption of whole milk with the formula was recommended.

Two weeks after the initiation of MSQ-11 supplementation, hemoptysis resolved. Shortly after completing the course, pneumonia developed specifically affecting the tumor site. Antibiotics were prescribed and the pneumonia subsequently resolved.

After the resolution of the pneumonia, the patient enjoyed a relatively uneventful three months before he was again admitted to the hospital on Oct. 13, 2000 with right-sided anterior chest pain, shortness of breath, dyspnea on exertion and peripheral edema.

His blood gases were $pO_2$ 5.59 kPa, $pCO_2$ 7.60 kPa, pH 7.383 and Sat 79.8%. A chest X-ray revealed the progression of the tumor in the upper right lobe as well as pleural fluid accumulation. Complete atelectasis of the right lung had developed. During pleurocentesis, 650 ml of fluid was removed which contained blood, large numbers of lymphocytes, macrophages and mesothelial cells. In the cytology report, there is no mention of tumor cells. Subsequently, he was released and instructed to return in the event if his dyspnea was worsening.

Five weeks later on Nov. 20, 2000, the patient was readmitted to the hospital with fever (37.7-38.8° C.), shortness of breath, and dyspnea on rest. His blood gases on admission were $pO_2$ 43, $pCO_2$ 52, pH 7.43 and Sat 79%. Chest x-ray revealed the progression of the upper right lobe tumor with an expansion into the central lobe. Complete atelectasis of the right lung and hydrothorax had developed. During another pleurocentesis, 800 ml of pleural fluid was removed. The pleural fluid contained large numbers of white blood cells. The general condition of the patient did not allow chemotherapy. At this point, the prognosis was extremely bleak.

At this time, a combination of Soma extract and MSQ-11 was given. One week after his second pleural drainage, the patient started taking 1 ml of Soma extract twice a day, dissolved in a cup of water (starting on Nov. 29, 2000). Soma was administered for six weeks. At three weeks into the Soma therapy, MSQ-11 was added to the regimen at 3 tbsp per day for one month. A maintenance dose of 1 tbsp of MSQ-11 a day was used for an additional month after completing this standard treatment course.

The patient's hypoxia was relieved with a nutritional supplement, called Aerobic 07 (Aerobic Life Industries, Phoenix, Ariz., USA). Aerobic 07 delivers oxygen directly into the circulation via the stomach. The dosage was 10 drops dispersed into a cup of water, taken twice a day, following the general recommendations of the manufacturer. The patient reported an immediate relief from his dyspnea upon taking the first dose of Aerobic 07. Four days later upon his discharge, the patient's blood oxygen saturation was 88%.

He continued using Aerobic 07 at the same dose for 4 months and for another 4 months at a half dose. The patient reported Aerobic 07 to be very important in improving his general well being. Repeated determination of oxygen saturation has shown a continuous progress.

On Jan. 3, 2001, the patient was readmitted to the hospital, and 350 ml of yellow pleural fluid was removed. Cytology found a few lymphocytes and macrophages with no blood or tumor cells present. This time it appeared that his pleuritis carcinomatosa was subsiding. Blood gases were $pO_2$ 7.06 kPa, $pCO_2$ 6.40 kPa, pH 7.462 and Sat 89.1%.

One week later on Jan. 10, 2001, ahead and chest CT was performed. No abnormalities were found inside the cranium. Abnormal lymph nodes were absent in the mediastinum. A circular constriction of the upper right lobar bronchus was observed. In the upper right lobe, tumorous infiltration was apparent. The size of the upper right lobe tumor could not be determined. The image suggested necrosis. Pleural fluid accumulation was noted but it was insufficient for tapping. He was released from the hospital.

From January the patient lived at home and reported a relatively good quality of life. On Mar. 26, 2001, the patient checked into the hospital because of chest pain. His blood gases-were pO$_2$ 8.73 kPa, pCO$_2$ 5.89 kPa, pH 7.421 and Sat 93.1%. The patients blood oxygen saturation had returned to normal. Chest x-ray found no tumor progression and pleural fluid was undetectable. The episode was diagnosed as viral infection.

Four months later, he was admitted to the hospital again because of right-sided chest pain. Chest x-ray has shown no change since his previous admission. An ultrasound exam found no abnormalities in the organs inside the abdomen. Results of any cardiac evaluation could not be found. The chest pain was attributed to scar tissue formation in the upper right lobe. He was given pain medication and released.

A month later, the patient was admitted to the hospital, this time with worsening signs of congestive heart failure. At the same time, chest x-ray showed progression of the upper right lobe tumor. Pleural fluid was undetectable. MSQ-11 administration was initiated. His cardiac functions continued to deteriorate and were not responding to therapy. Three weeks later, he deceased. At the family's request, no autopsy was performed.

Discussion

Lung cancer can be linked to tobacco smoking in the majority of cases (Doll, R, Gray R, Hafner B, and Peto R. Br Med J 280: 961-971, 1980; Doll R and Hill A. Br Med J 2: 1071-108 1, 1956). Despite the great expansion of understanding cancer biology, lung cancer remains one of the deadliest human neoplasias. About 90% of lung cancer patients die due to the worst cure rates among common solid tumors ("Cancer Facts and Figures2000." 2000 American Cancer Society, Atlanta). New therapeutic strategies are therefore needed that can improve current prospects for long-term survival from lung cancer.

In this Example, we presented a patient's case with rapidly progressing, large, partially undifferentiated squamous cell carcinoma (Marchevsky A M. Malignant epithelial tumors of the lung. In: Marchevsky A M, ed. Surgical pathology of lung neoplasms. N.Y., Marcel Dekker, 1990:77-229) and demonstrated the resolution of carcinomatous pleuritis and atelectasis developed during the progression of his carcinoma. The patient had a history of emphysema and acute myocardial infarction. His critical condition and the bleak prognosis of his disease qualified him for this alternative approach.

The progression of the tumor discontinued and the pleuritis carcinomatosa resolved over a period of 2 months while using a combination of Soma and MSQ-11. The patient reported a gradual increase in his energy and an overall improvement in the quality of his life that lasted for nearly 8 months. He experienced no side effects during Soma and MSQ-11 administration. Additional oral oxygenation was effective in relieving the patients dyspnea and improved oxygenation may have contributed to the overall effects of Soma and MSQ-11.

This study described how the administration of a combination of natural remedies coincided with the regression of an originally inoperable lung carcinoma. We believe that this therapeutic modality will have a similar beneficial effect for all cancers including carcinomas, sarcomas and lymphomas.

EXAMPLE 2

Tumor Regression in a Recurrent, Metastatic Squamous Cell Carcinoma of the Cervix: Case Report Cervical carcinoma is a common gynecological neoplasia that caused 4,100 deaths in 2002 in the United States (1). Radical pelvic surgery and radiation therapy is the mainstay in treatment (2). Chemotherapy is generally reserved for treatment of locally recurrent disease (3,4). Despite advances in surgical techniques, radiation, and chemotherapy, stage-specific survival rates of patients with locally advanced cervical cancer have not improved (2,5). Therefore, it is important to develop new treatment modalities in order to improve current prospects for long-term survival.

In this report, a patient's case is presented with a recurrent, metastatic squamous cell carcinoma of the cervix. The report demonstrates that a novel, nutritional combination therapy produced tumor regression and no evidence of disease.

Methods

In June 1998, a 43 year-old patient was diagnosed with squamous cell carcinoma of the cervix (grade II/A) and metastasis to the colon. She underwent Wertheim's radical hysterectomy and pre- and post-operative radiation therapy for a total dose of 50 Gy.

In June 2000, she was diagnosed with right-sided hydronephrosis, rectovaginal fistula, and recurrent malignant disease in the pelvis. Rectovaginal exam confirmed a 6-cm tumor that was partially attached to the pelvic wall and infiltrated the base of the bladder as well as the colon. In July 2000, 6 cycles of the Cysplatin-Vepesid-Epirubicin combination chemotherapy was initiated. She received 2 cycles of chemotherapy (one each in July and August). Because of the serious side effects of the treatment (myelosuppression, nausea, vomiting and severe pain in the flanks and extremities) no further chemotherapy was administered and the patient received only red blood cell transfusions and pain medication from that on. Her prognosis was poor.

Starting in the beginning of November 2000, the patient has taken a one month long course of MSQ-11. This formula was established based on the analysis of the scientific literature on the effects of nutrition on a variety of cancers (6). The active ingredients are blackstrap molasses, apple cider vinegar, quinine and sulfur. The dosage was 1 tbsp TID po taken with meals until 1 quart (946 ml) of the mixture was consumed, then 1 tbsp QD for another 5 months. Ample consumption of whole milk or purified water with the formula is recommended.

Besides MSQ-11, Soma a healing herb described in the sacred scriptures of the Hindis, the Rig Veda (7) was also administered. Soma is credited with healing powers in a variety of diseases. Soma extract was prepared following the directions in the 9th Book of Rig Veda.

The dosage for Soma was 1 ml of extract QD po, taken in a cup of water and administered for 4 weeks. Subsequently, it was taken every other day. Shortly after starting on these nutritional supplements, the patient reported an improvement in her appetite and general well being. She started gaining weight. The clinical manifestations of neuropathy have subsided and the myelosuppression, as evidenced by normal CBC, disappeared. Her other blood test results normalized and rectovaginal exams demonstrated the regression of the tumor. The patient was monitored periodically by clinical examinations and by May 2001 no tumor could be detected clinically or otherwise. In September 2001, the patient underwent an ileus surgery and the preparation of a temporary preternatural anus.

The patient remained stable until January 2002, when she presented with high fever and right flank pain. This was attributed to a urinary infection caused by the yet unresolved rectovaginal fistula. Abdominal ultrasound exam has shown a right-sided renal abscess, the resolution of which required right-sided nephrectomy. In March 2002, an abdominal CT exam has shown an irregularly shaped growth in the right side of the pelvis that has accumulated contrast material and was in contact with the base of the bladder as well as the adjacent intestines.

A gynecological exam in April 2002 has found a mass around the vaginal cuff that filled the entire pelvis area and was suspected to be a recurrent tumor. Pathological exam has shown the recurrence of SCC of the cervix (grade III-IV). The tumor was evaluated to be inoperable. In the same month, the surgical repair of the rectovaginal fistula was carried out. At this point, she has resumed taking MSQ-11 and Soma. Soma was administered at the same dosage as in 2001 while the dosage of MSQ-11 was 2 tbsp TID. The tumor regression was monitored by pelvic ultrasound, and clinical examinations. Subsequently, the nutritional supplement regime was adapted according to the clinical status and ultrasound results.

In May 2002, an ultrasound exam has shown a highly vascularized, 41×53×60 mm size tumor in the right side of the pelvis that has infiltrated the wall of the bladder. Thus, a more active formula, MSQ-11A that also contained vitamin $B_{12}$ and rose oil was administered instead of MSQ-11 at 2 tbsp TID. The use of Soma was discontinued.

In June 2002, an ultrasound exam has shown a 40×27×28 mm size tumor in the right side of the pelvis that was attached to the bladder over an area of 2 cm diameter and to the colon over an area of 1.7 cm diameter. A subsequent CT exam has shown the adhesion of intestinal loops to the base and the right side of the bladder. Inside the conglomerate, a 3 cm diameter solid formation was found that was thought to be the tumor.

An ultrasound exam in July 2002, has demonstrated a 30×33×60 mm size irregular-shaped formation in the right side of the pelvis. To potentially accelerate tumor regression, MSQ-11A was replaced with the more active MSQ-13 formula. MSQ-13 contains folic acid and molecular iodine as additional components. After completing the basic course of MSQ-13 therapy (2 quarts), a pelvic hemorrhagic episode occurred. Large blood clots were spontaneously discharged rectally and vaginally. The surgical team interpreted this as possible healing process. The anemia caused by the hemorrhage resolved without a need for intervention. The patient continued with the nutritional supplementation. Subsequent ultrasound exam has found an 8×5 cm formation in the right side of the pelvis. The enlargement was probably caused by the hemorrhage.

A CT exam in late September 2000 has found an irregular-shaped soft tissue conglomerate in the right side of the pelvis that was attached to the right side of the bladder. Above the vaginal fornix, a 4-5 cm-size solid formation was found. The oral contrast material accumulated inside the vagina (vaginal tampon) indicating the presence of a still existing fistula. No accumulation of contrast material was observed elsewhere. Abnormal lymph nodes were absent in the retroperitoneum. An MRI exam was prescribed to differentiate the tumor from the surrounding scar tissue.

Subsequent to the hemorrhage, the patient noticed a gradually intensifying inflammation in her pelvis by early October 2002. On multiple occasions, spontaneous putrid smelling vaginal and rectal discharges occurred that were accompanied with episodes of fever (37-38° C.). After a gynecological exam and a CT scan in November 2002, she was referred to emergency surgery during which an about 12 cm size abscess was drained in the lower abdomen. The examination of the surrounding area indicated a potential continuation of the abscess. A lower pelvic laparotomy was performed that opened another, larger abscess that stretched from behind the symphysis towards the vaginal cuff. Following the lysis of small bowel adhesions, an encapsulated 3.5×5 cm size tumor, extensively attached to the sacrum, was observed. No metastases were found in the abdominal cavity.

The small bowel fistula could not be repaired at this time and the patient was scheduled for another surgery in February 2003. The fistula repair was attempted at the end of February 2003; however it turned out to be unsuccessful. Another surgery was performed in the middle of April 2003 to close the fistula but, again, it was unsuccessful. The patient deceased at the end of April 2003. No autopsy was performed at the family's request.

Discussion

Survival for woman with cervical cancer has improved over the years primarily because of early diagnosis. For advanced disease, the 5-year survival rates remain unchanged (2,5). The 31% survival for stage III and 8% for stage IVA disease indicates that radiotherapy is not an effective therapeutic modality. Chemotherapy has been used for the management of locally recurrent disease but objective and subjective responses are of short duration (4,5). The prognosis for recurrent, locally advanced cervical carcinoma is poor.

This case study demonstrates that a combination of nutritional supplements may offer an effective tool for the management of recurrent SCC of the cervix. This patient's critical condition and her poor prognosis qualified her for this alternative approach.

This paper describes a non-toxic, nutritional therapy that was established based on the analysis of the scientific literature on the effects of nutrition on a variety of cancers (6). This analysis led to the conclusion that nutrition can provide a unifying perception of cancer and recast it as a single disease potentially treatable by a single protocol.

Nutritional deficiencies of plant-derived phenolic compounds, lipids, vitamins and minerals have been identified in a variety of cancers (6). Based on these, it was hypothesized that the supplementation of these nutrients of adequate amounts to cancer patients might reverse the course of the disease as human cells do have the capacity of self-repair.

During the first recurrence of the disease, a combination of Soma and MSQ-11 was administered at a low dosage over a time period of several months. This cautious dosage regimen was warranted by the fact that she had come out of chemotherapy with right-sided renal failure, myelosuppressed and neuropathic. Her general condition was very weak in the beginning of nutritional supplementation. Shortly after the initiation of supplementation, her appetite returned and over a time period of 2 months, she has regained all her lost weight. Myelosuppression and neuropathy have resolved. Her general condition improved such that she has resumed her daily routines. Clinical data confirmed tumor regression and subsequently has shown no evidence of disease. She has experienced no side effects during administration of nutritional supplementation.

The unresolved rectovaginal fistula, a frequent combined side effect of disease and intensive pelvic radiation therapy, led to serious complications. A renal abscess developed, the resolution of which required right-sided nephrectomy. A satisfactory recovery allowed the subsequent repair of the rectovaginal fistula. Pathological exam confirmed a recurrence of SCC of the cervix, which this time has infiltrated the colon and the bladder.

The patient has resumed taking Soma and MSQ-11 that later on was replaced with the more active MSQ-11A and MSQ-13. Tumor regression of greater than 50% and the resolution of metastases were observed during the course of her second alternative treatment. Her general condition was fair. The patient has undergone three surgeries in 2002 and two more in 2003 in an attempt to repair the active fistulas. Unfortunately, the conditions of her bowels have made the repair attempts unsuccessful and the patient deceased despite all the improvements in her oncological status.

Further studies are warranted to investigate the utility of this nutritional approach in a larger population of cervical cancer patients.

REFERENCES

1. "Cancer Facts and Figures—2002." American Cancer Society, Atlanta 2002.
2. Thar T, Milton R R, Daily J W: Radiation treatment of the carcinoma of the cervix. Semin Oncol 9; 299-311, 1982.
3. DeVita V T, Wasserman T H, Young R C: Perspectives in research in gynecologic oncology. Cancer 38; 509-525, 1991.
4. Alberts D S, Garcia D, Mason-Liddil N: Cysplatin in advanced cancer of the cervix: An update. Semin Oncol 18; 11-24, 1991.
5. Petterson F (ed.): Carcinoma of the uterine cervix. In: Annual report on the results of treatment in gynecological cancer. FIGO 22; 51-63, 1994.
6. Grandics P: submitted for publication.
7. Griffith R T H: The hymns of the Rigveda, Shastri, J L ed. Delhi, Motilal Banarsidass Publishers, 1999.

While the specification describes particular embodiments of the present invention, those of ordinary skill can devise variations of the present invention without departing from the inventive concept.

We claim:

1. A therapeutic composition for the treatment of cancer comprising:
   (a) an aqueous extract of the plant Soma, the plant Soma being identified as *Asclepias tuberosa*, the aqueous extract being preserved with salt; and
   (b) a mixture of milk, plant derivatives and a mineral comprising:
      (i) apple cider vinegar;
      (ii) quinine;
      (iii) blackstrap molasses;
      (iv) sulfur; and
      (v) whole milk;
   wherein the aqueous extract of Soma, the apple cider vinegar, the quinine, the blackstrap molasses, and the sulfur are each present in a sufficient quantity so that the resulting composition has a therapeutic effect against cancer.

2. The composition of claim 1 wherein the composition further comprises ground red pepper, corn oil, pineapple juice, and raw almonds.

3. The composition of claim 1 wherein the composition further comprises iodine.

4. The composition of claim 1 wherein the composition further comprises Vitamin $B_{12}$ and rose petal extract/rose oil.

5. The composition of claim 4 wherein the composition further comprises folic acid.

6. The composition of claim 1 wherein the mixture of plant derivatives and a mineral comprises about 6.23% (v/v) of apple cider vinegar, about 0.317% (w/v) of quinine, about 79.8% (v/v) of blackstrap molasses, and about 3.1% (w/v) of sulfur.

7. The composition of claim 1 wherein the aqueous extract of the plant Soma is prepared from roots of the plant Soma that had been steeped in boiling water for about 20 minutes to inactivate potentially toxic proteins.

8. A therapeutic composition for the treatment of cancer comprising:
   (a) an aqueous extract of the plant Soma, the plant Soma being identified as *Asclepias tuberosa*, the aqueous extract being preserved with salt; and
   (b) a mixture of water, plant derivatives and a mineral comprising:
      (i) apple cider vinegar;
      (ii) quinine;
      (iii) blackstrap molasses;
      (iv) sulfur; and
      (v) water;
   wherein the aqueous extract of Soma, the apple cider vinegar, the quinine, the blackstrap molasses, and the sulfur are each present in a sufficient quantity so that the resulting composition has a therapeutic effect against cancer.

9. The therapeutic composition of claim 8 wherein the aqueous extract of the plant Soma is prepared from roots of the plant Soma that had been steeped in boiling water for about 20 minutes to inactivate potentially toxic proteins.

10. A method for treatment of cancer comprising administering an effective amount of the composition of claim 1 to a patient in need of treatment thereof.

11. A method for treatment of cancer comprising administering: (a) an effective amount of the composition of claim 2; and (b) aspirin, to a patient in need of treatment thereof.

12. A method for treatment of cancer comprising administering an effective amount of the composition of claim 3 to a patient in need of treatment thereof.

13. A method for the treatment of cancer comprising administering an effective amount of the composition of claim 4 to a patient in need of treatment thereof.

14. A method for the treatment of cancer comprising administering an effective amount of the composition of claim 5 to a patient in need of treatment thereof.

15. A method for the treatment of cancer comprising administering an effective amount of the composition of claim 6 to a patient in need of treatment thereof.

16. A method for the treatment of cancer comprising administering an effective amount of the composition of claim 7 to a patient in need of treatment thereof.

17. A method for the treatment of cancer comprising administering an effective amount of the composition of claim 8 to a patient in need of treatment thereof.

18. A method for the treatment of cancer comprising administering an effective amount of the composition of claim 9 to a patient in need of treatment thereof.

19. The method of claim 10 wherein the cancer is a malignancy of the lymphoid system.

20. The method of claim 11 wherein the cancer is a malignancy of the lymphoid system.

21. The method of claim 12 wherein the cancer is a malignancy of the lymphoid system.

22. The method of claim 13 wherein the cancer is a malignancy of the lymphoid system.

23. The method of claim 14 wherein the cancer is a malignancy of the lymphoid system.

24. The method of claim 16 wherein the cancer is a malignancy of the lymphoid system.

25. The method of claim 17 wherein the cancer is a malignancy of the lymphoid system.

26. The method of claim 18 wherein the cancer is a malignancy of the lymphoid system.

27. The method of claim 10 wherein the composition is used in conjunction with chemotherapy and relieves chemotherapy-associated nausea or vomiting.

28. The method of claim 11 wherein the composition is used in conjunction with chemotherapy and relieves chemotherapy-associated nausea or vomiting.

29. The method of claim 12 wherein the composition is used in conjunction with chemotherapy and relieves chemotherapy-associated nausea or vomiting.

30. The method of claim 13 wherein the composition is used in conjunction with chemotherapy and relieves chemotherapy-associated nausea or vomiting.

31. The method of claim 14 wherein the composition is used in conjunction with chemotherapy and relieves chemotherapy-associated nausea or vomiting.

32. The method of claim 16 wherein the composition is used in conjunction with chemotherapy and relieves chemotherapy-associated nausea or vomiting.

33. The method of claim 17 wherein the composition is used in conjunction with chemotherapy and relieves chemotherapy-associated nausea or vomiting.

34. The method of claim 18 wherein the composition is used in conjunction with chemotherapy and relieves chemotherapy-associated nausea or vomiting.

* * * * *